US00PP26526P3

(12) United States Plant Patent
Martinavarro

(10) Patent No.: US PP26,526 P3
(45) Date of Patent: Mar. 22, 2016

(54) MANDARIN TREE NAMED 'GCM 305'

(50) Latin Name: *Citrus reticulata*
Varietal Denomination: GCM 305

(71) Applicant: GCM VARIEDADES VEGETALES A.I.E., Almazora, Castellón (ES)

(72) Inventor: Fernando Ballester Martinavarro, Sollana (ES)

(73) Assignee: GCM VARIEDADES VEGETALES A.I.E., Almazora, Castellón (ES)

( * ) Notice: Subject to any disclaimer, the term of this patent is extended or adjusted under 35 U.S.C. 154(b) by 323 days.

(21) Appl. No.: 13/986,574

(22) Filed: May 16, 2013

(65) Prior Publication Data

US 2014/0345012 P1 Nov. 20, 2014

(51) Int. Cl.
*A01H 5/08* (2006.01)

(52) U.S. Cl.
USPC ..... Plt./202
CPC ..... *A01H 5/0806* (2013.01)

(58) Field of Classification Search
USPC ..... Plt./202, 201
CPC ..... A01H 5/0806; A01H 5/08
See application file for complete search history.

*Primary Examiner* — Kent L Bell
(74) *Attorney, Agent, or Firm* — Westerman, Hattori, Daniels & Adrian, LLP

(57) ABSTRACT

'GCM 305' is a late-season maturing mandarin obtained by partial cross of the 'KARA' mandarin in Huelva, Spain. 'GCM 305' has medium-sized fruit which is essentially seedless and has good storage characteristics. The fruit is easy to peel, has a smooth rind texture, a dark orange color, a very rich sweet flavor, and a pleasant aroma.

4 Drawing Sheets

Latin name of the genus and species: The mandarin cultivar of this invention is botanically identified as *Citrus reticulata* hybrid.

Variety denomination: The variety denomination is 'GCM 305'.

BACKGROUND OF THE INVENTION

The invention relates to a new and distinctive mandarin hybrid cultivar designated 'GCM 305', which was developed in Huelva, Spain.

BRIEF SUMMARY OF THE INVENTION

'GCM 305' is a late-season maturing mandarin variety having medium-sized fruit which is essentially seedless and has a rich flavor.

'GCM 305' is distinguished from other cultivars known to the inventor in that it produces fruit that combine late-season maturity and medium size with an absence of neck. The fruit is easy to peel, has a smooth rind texture, a dark orange color, a very rich sweet flavor, and a pleasant aroma.

BRIEF DESCRIPTION OF THE DRAWINGS

The figures depict various characteristics of 'GCM 305'.

DETAILED DESCRIPTION

Figure 1:
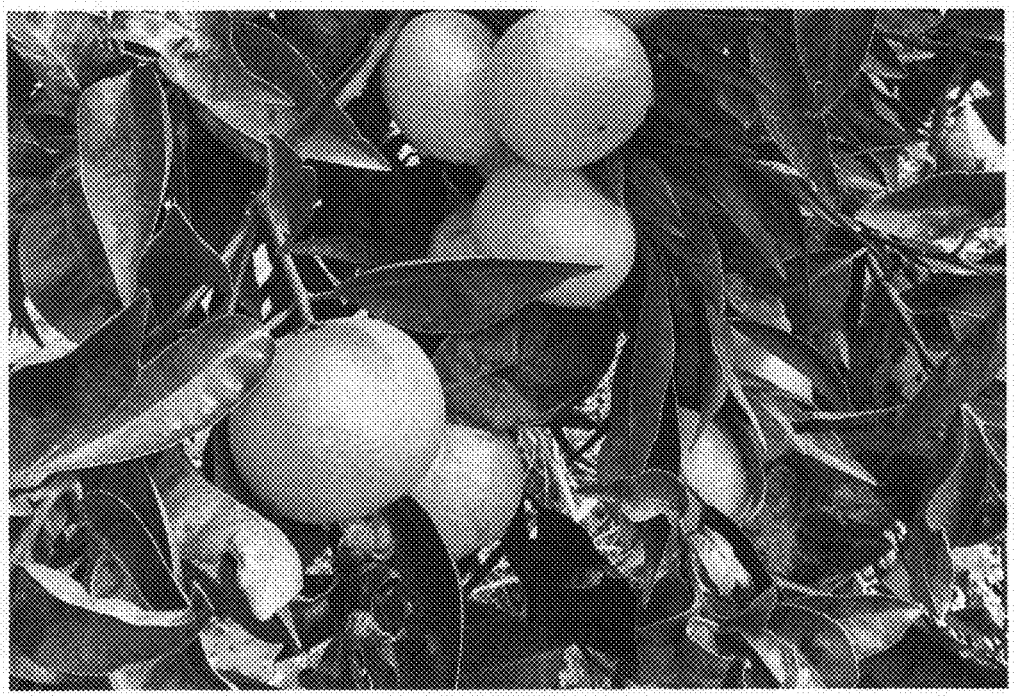
FIG. 1 shows fruit and foliage of 'GCM 305' taken at Huelva in February 2013.
Figure 2:
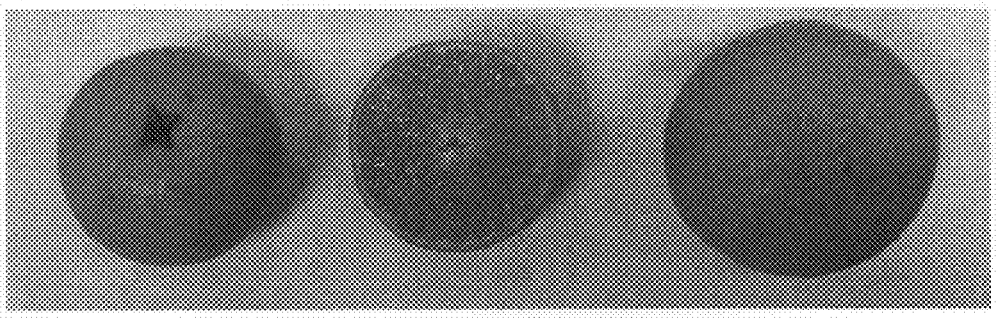
FIG. 2 shows a cross-section of 'GCM 305' fruit.
Figure 3:
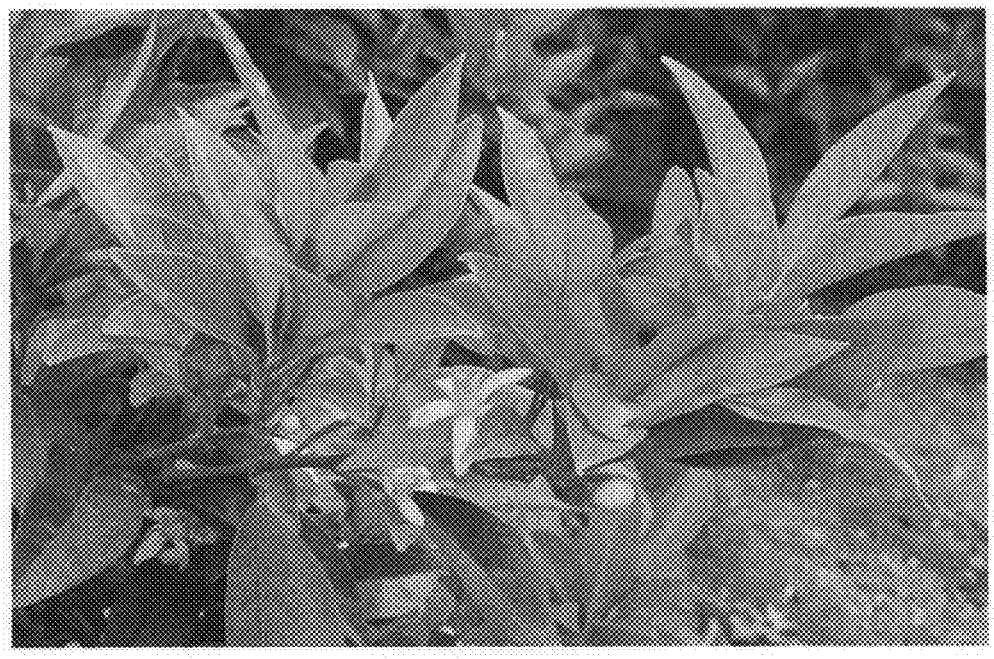
FIG. 3 shows the 'GCM 305' flowers.
Figure 4:
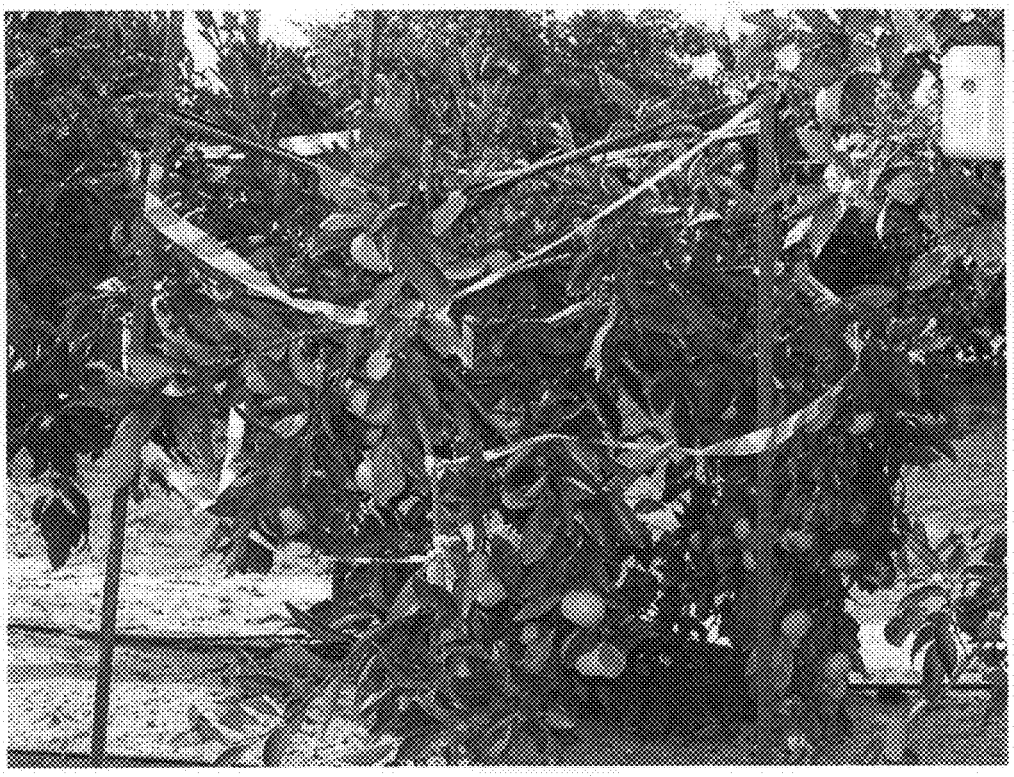
FIG. 4 shows a two-year-old 'GCM 305' mandarin tree grafted on a five years *Carrizo citrange* rootstock.

'GCM 305' was obtained by partial cross in Huelva, Spain, of the 'KARA' mandarin (unpatented), which is a diploid of

*C. unshiu*×*C. nobilis* (*Citrus reticulata* Blanco). The fruit was collected in December 2007, and seeds of the fruit were extracted and subsequently germinated during January 2008. About 350 seedlings were grown from the germinated seeds. Each seedling was grafted in March 2009 onto two-year-old *Citrus macrophylla* rootstocks that had been planted in 10-liter pots.

The grafted plants were cultivated and the first fruit were observed in January 2012. Observations of the fruits were made again in 2013. One of these 350 seedling was designated 'GCM 305'.

An important characteristic of 'GCM 305' is that it is essentially seedless.

Studies of hand cross-pollination were made between 'GCM 305' and other seeded and seedless varieties. For each combination, 'GCM 305' was used as a female parent and as pollinator. The studies showed that self-pollinated 'GCM 305' is seedless, whereas the parent variety 'KARA' is seeded.

'GCM 305' is a late-maturing variety like its parent 'KARA', but unlike 'KARA' the 'GCM 305' variety has seedless fruit.

All color descriptions herein are by reference to the color chart of The Royal Horticultural Society (R.H.S.)

Tree size and growth characteristics:

*Size of tree.*—Medium sized. A typical two-year-old tree is 1.80 meters high by 1.60 meters wide. A typical trunk diameter in a three-year-old rootstock is 4 cm at 9 cm above the ground.

*Shape of tree.*—Spheroid, erect-drooping similar to 'KARA'.

*Growth characteristic.*—Vigorous growth.

*Surface.*—The trunk has a smooth surface texture and is greyed-brown in color (RHS 197A).

*Branch.*—On average, the branches has a circumference of 1.2 cm. There are also, on average, three main branches per tree, each having an average crotch angle of 55°. As with the trunk, the branches have a smooth surface texture and are greyed-brown in color (RHS 197A).

*Internode length.*—5 cm on average.

*Branch flexibility.*—Very flexible. Growing shoots have a smooth surface texture, a circumference of 1.2 cm, strong growth and a length of 80 cm to 120 cm. They are medium green in color (RHS 147A) and are at angle of 65°. Dormant shoots have a smooth surface texture, a circumference of 1-1.2 cm, a length of 60 cm to 80 cm. They are greyed-brown in color (RHS 197A). and are at angle of 55°.

Leaves:

*Shape.*—Lanceolate.

*Apex.*—Acute.

*Margins.*—Slightly crenate.

*Color and surface texture.*—The adaxial (upper) leaf surface is medium green in color (RHS 147A) and the abaxial (lower) leaf surface is yellow green (RHS 146A). The leaf has venation consisting of a cross-linked network formed by anastomosis of the vascular bundles, in which smaller veins diverge from the larger ones. The vascular system of the leaf is distinguished by a prominent mid-vein (yellow green RHS 146A). Most of the major side branch veins (medium green RHS 147A) near the edge form a Y shape. Every branch vein anastomoses with the other lateral veins. In the abaxial surface veins are medium green (RHS 147A). The leaf upper surface is smooth while leaf veins are prominent on the leaf lower surface.

*Bearing.*—Evergreen.

*Size.*—Usually about 11.3 cm in length on average, and about 5.2 cm in width, on average. The leaves are at an average angle of 45° with the branches, and are separated by 5 cm from each other, on average.

*Buds.*—Are located on the petiole base; are round, 1.5 mm in diameter, 0.5 mm in length, and yellow-green (RHS 146A).

*Petioles.*—No wing on the petiole. Usually about 13.6 mm in length on average, and 1.5 mm in width, on average.

Thorns: None.

Flowers:

*Flower buds.*—Ovoid is shape, with an average length of 11.6 mm, and an average width of 5 mm.

*Opened flower.*—Average length of 32 mm, with a typical calyx diameter of 5.8 mm, and a typical citrus flower fragrance.

*Time of flowering.*—Early April in Huelva, Spain.

*Type of flower.*—Hermaphrodite.

*Color of open flower.*—White (RHS 155C) with coloring (RHS 158B) on the lower side of petals.

*Flower grouping.*—Solitary in a raceme arrangement at axillary and terminal positions.

*Number of petals.*—5 to 6.

*Petals.*—Smooth and elliptic in shape, with an average length of 13.4 mm and an average width of 6 mm. The petal tip is acute in shape, while the base is truncate. The margin is entire.

*Number of anthers.*—18-20.

*Color of anthers.*—Light yellow (RHS 8C).

*Number of sepals.*—5.

*Sepals.*—Basally connate, with smooth margin, medium green (RHS 147A) in both surfaces, with average length of 3 mm.

*Pedicels.*—Usually about 8.2 mm in length on average, and 1.2 mm in width on average, medium green (RHS 147A).

*Reproductive organs.*—The style has a length of 7.7 mm, while the style and the stigma are approximately 9 mm long. The stamen has a length of 10.8 mm, the color being RHS 155C. On average there is one style and one stigma, and 18 stamens with anthers. Pistil number is one (stigma+style+ovary). The ovary is round, on average 2.4 mm, and yellow green (RHS 146A).

*Pollen.*—Fertile. The pollen color is yellow-orange (RHS 15C). Degree of germination unknown.

Fruit:

*Time of fruit harvest.*—Early February in Huelva, Spain.

*Shape.*—Obloid.

*Albedo.*—2.2 mm on average, white in color (RHS 155C).

*Diameter.*—76 mm, on average.

*Length.*—53 mm, on average.

*Weight.*—128 grams, on average.

*Rind.*—Medium orange (RHS 30B), with medium number of oil glands. Thickness of rind at maturity is 2.5-3 mm.

*Ease of separation of rind from fruit at maturity.*—Medium.

*Flesh.*—Medium orange (RHS 28A), with fine texture.

*Axis at maturity.*—Medium.

*Number of segments in a fruit.*—9-10, well-developed segments per fruit, with a medium coherence of adjacent wall segments, and elongated juice vesicles of medium thickness.

*Length.*—85 mm on average.

*Width.*—47 mm on average.

*Under self-pollination conditions.*—Fruit are seedless.

*Acidity/sweetness.*—1% acid content/13° Brix.

*Degree of juiciness.*—51%.

*Fruit production.*—Begins at 2-3 years.

*Storage characteristics.*—Good for washed but unwaxed fruit. Also good for waxed fruit. No loss of rind quality or color, no loss in juice quality or deterioration in taste observed upon storage. Quality of fruit well retained upon storage. No indication of fungal or other disease upon storage.

Disease/pest resistance/susceptibility:

*Resistance to disease.*—Tolerant to *Citrus Tristeza* (CTV) and *Alternaria* spp., from observation to date.

*Resistance to pests.*—Is susceptible to aphids. mites, and scales that are commonly present with mandarin trees.

*Winter hardiness.*—Similar to that of the parental.

*Resistance to heat.*—Similar to that of the parental.

The invention claimed is:

1. A new and distinct mandarin tree having the characteristics substantially as described and illustrated herein.

* * * * *